(12) United States Patent
Palme et al.

(10) Patent No.: US 10,172,638 B2
(45) Date of Patent: Jan. 8, 2019

(54) MULTIPLE FUNCTION VASCULAR DEVICE

(71) Applicant: Device Source, LLC, Lindstrom, MN (US)

(72) Inventors: Robert A. Palme, Lindstrom, MN (US); Gregory L. Townsend, Motley, MN (US)

(73) Assignee: DEVICE SOURCE, LLC, Lindstrom, MN (US)

( * ) Notice: Subject to any disclaimer, the term of this patent is extended or adjusted under 35 U.S.C. 154(b) by 99 days.

(21) Appl. No.: 15/089,103

(22) Filed: Apr. 1, 2016

(65) Prior Publication Data

US 2016/0270814 A1    Sep. 22, 2016

Related U.S. Application Data

(63) Continuation of application No. 12/803,284, filed on Jun. 23, 2010, now abandoned.

(51) Int. Cl.
| | | |
|---|---|---|
| *A61B 17/3207* | (2006.01) | |
| *A61B 17/00* | (2006.01) | |
| *A61B 17/22* | (2006.01) | |
| *A61B 90/00* | (2016.01) | |

(52) U.S. Cl.
CPC ........... *A61B 17/320758* (2013.01); *A61B 17/00234* (2013.01); *A61B 2017/00305* (2013.01); *A61B 2017/00323* (2013.01); *A61B 2017/00867* (2013.01); *A61B 2017/22079* (2013.01); *A61B 2090/08021* (2016.02)

(58) Field of Classification Search
CPC  A61B 2017/00867; A61B 2017/22079; A61B 2017/00323; A61B 2017/00305; A61B 2090/08021; A61B 17/320758; A61B 17/00234; A61N 2090/08021
See application file for complete search history.

(56) References Cited

U.S. PATENT DOCUMENTS

| | | |
|---|---|---|
| 3,973,556 A | 8/1976 | Fleischhacker |
| 4,798,598 A | 1/1989 | Bonello et al. |
| 4,813,434 A | 3/1989 | Buchbinder et al. |
| 4,815,478 A | 3/1989 | Buchbinder et al. |
| 4,940,062 A | 7/1990 | Hampton et al. |
| 5,037,391 A | 8/1991 | Hammerslag et al. |
| 5,060,660 A | 10/1991 | Gamble et al. |
| 5,120,308 A | 6/1992 | Hess |
| 5,125,895 A | 6/1992 | Buchbinder et al. |
| 5,203,772 A | 4/1993 | Hammerslag et al. |

(Continued)

OTHER PUBLICATIONS

International Search Report and Written Opinion of International Application No. PCT/US2011/001119, dated Oct. 20, 2011, 9 pages.

*Primary Examiner* — Kevin C Sirmons
*Assistant Examiner* — Tiffany Legette-Thompson
(74) *Attorney, Agent, or Firm* — Holzer Patel Drennan

(57) ABSTRACT

A multi-purpose vascular device defines a lumen allowing fluid communication there through and has a coil with a side of the coil winds having solid physical connections between the coil winds to prevent the connected coil wind side from expanding following the application of force by an actuating member which causes the connected coil winds to have a predetermined configuration in an unstressed state. The application of longitudinal force causes the unconnected coil winds to expand, resulting in the vascular device assuming a different configuration.

16 Claims, 18 Drawing Sheets

(56) References Cited

U.S. PATENT DOCUMENTS

| | | |
|---|---|---|
| 5,211,636 A | 5/1993 | Mische |
| 5,372,587 A | 12/1994 | Hammerslag et al. |
| 5,378,234 A * | 1/1995 | Hammerslag ..... A61M 25/0053 138/129 |
| 5,480,382 A | 1/1996 | Hammerslag et al. |
| 5,824,031 A | 10/1998 | Cookston et al. |
| 6,056,702 A | 5/2000 | Lorenzo |
| 6,059,739 A | 5/2000 | Baumann |
| 6,093,157 A | 7/2000 | Chandrasekaran |
| 6,126,649 A | 10/2000 | VanTassel et al. |
| 6,146,338 A | 11/2000 | Gardeski et al. |
| 6,776,765 B2 | 8/2004 | Soukup et al. |
| 7,481,778 B2 | 1/2009 | Cedro et al. |
| 2004/0102719 A1 | 5/2004 | Keith et al. |
| 2004/0236215 A1 * | 11/2004 | Mihara ............. A61M 25/0068 600/434 |
| 2006/0089569 A1 | 4/2006 | Soukup et al. |
| 2009/0043299 A1 * | 2/2009 | Racz ................. A61B 17/3401 606/41 |
| 2009/0082723 A1 | 3/2009 | Krogh |
| 2009/0131948 A1 | 5/2009 | Liu et al. |
| 2011/0319905 A1 | 12/2011 | Palme et al. |

\* cited by examiner

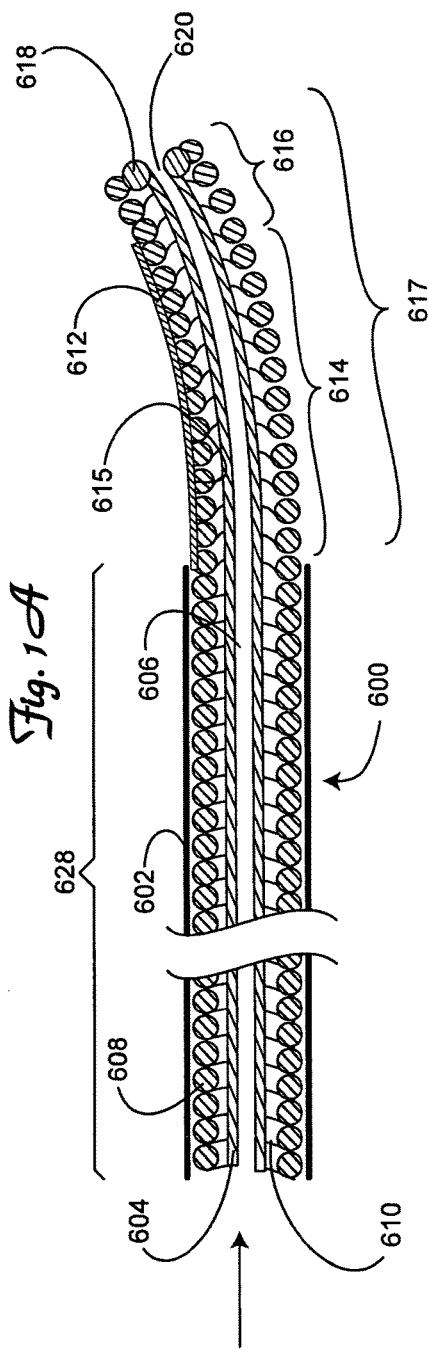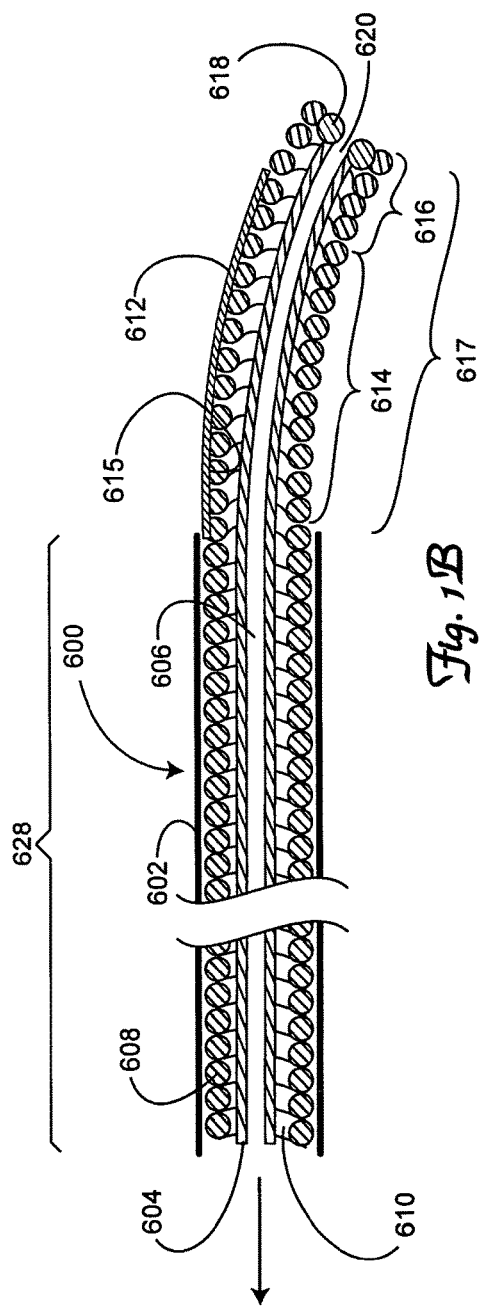

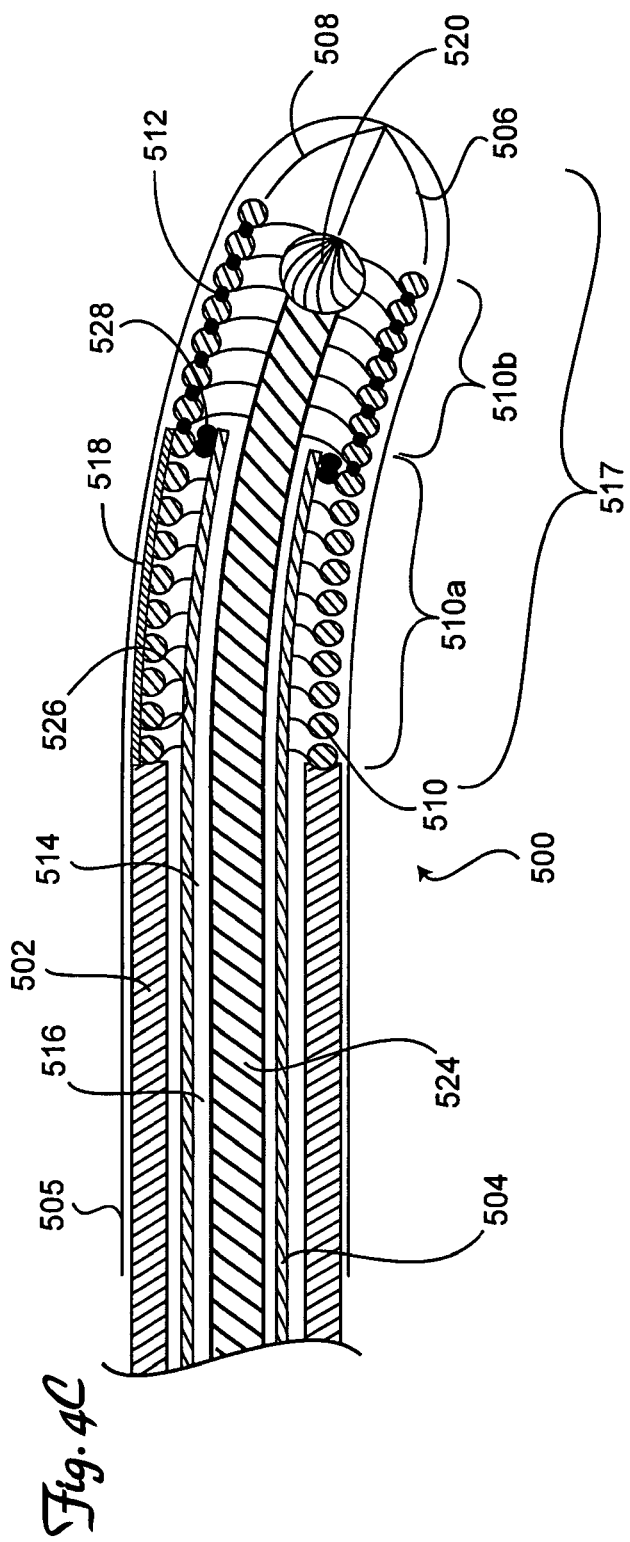

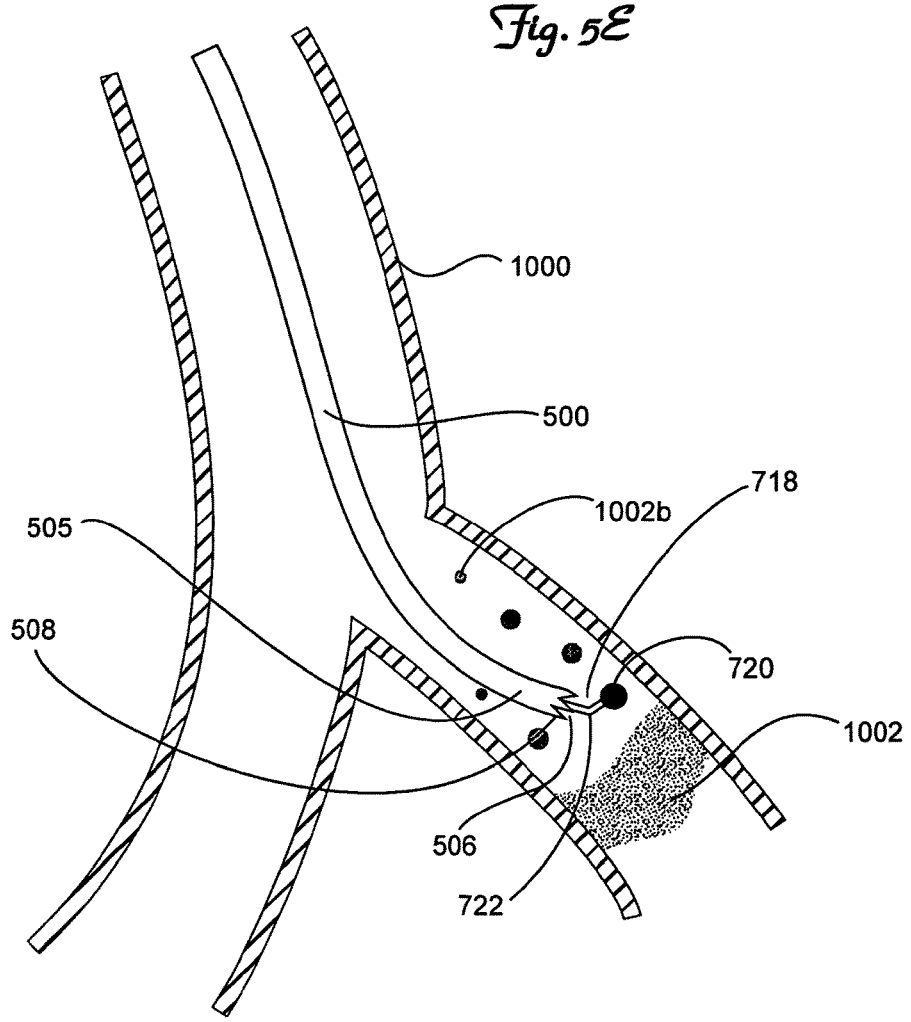

MULTIPLE FUNCTION VASCULAR DEVICE

CROSS-REFERENCE

This application is a continuation of U.S. application Ser. No. 12/803,284, filed Jun. 23, 2010, the entire disclosure of which is incorporated herein for all purposes.

FIELD OF THE INVENTION

The present invention relates to apparatus and methods for performing surgical procedures that access hollow conduits of mammalian anatomy. More particularly, the invention discloses a multi-function device for navigating tortuous vascular pathways, reaching and then crossing total occlusions in blood vessels.

BACKGROUND

Intracorporal medical devices have been developed and used to navigate and access the tortuous vascular and other hollow conduits of a mammalian body. Some of these devices include guidewires, catheters, intravenous guidewires, stylets, intravenous catheters and related devices like endoscopes and colonoscopes that have a predetermined degree of flexibility and may have straight or pre-formed, shaped ends to guide the device through the anatomical conduit. Of the devices that are employed to reach vascular blockages, each has certain advantages and disadvantages. Many fall short of desired performance before reaching a vascular blockage because of a device prolapse at a vascular bifurcation, an inability to enter a bifurcation or be directed to the site of therapy. Others may reach an occlusion but then require a different device to be introduced before crossing the stenosis. The medical industry has striven to reach a balance between the flexibility required to negotiate around tortuous pathways and the rigidity necessary to stabilize a catheter's advancement. Many products such as intravenous interventional guidewires provide directability, flexibility or stiffness but fail to do all or a combination at the same time. These products typically have pre-formed flexible distal ends that provide minimal directability but not true directability, flexibility and stiffness combined, which would be the most useful advantage. Additionally, most physicians must use a series of different diameter guidewires to perform one procedure, creating a procedure that costs additional time, money and risks patient safety from vascular injury.

Accessing occlusions having relatively sharp angles and passage constrictions using conventional guidewires having pre-formed "J" shapes or angled distal ends requires rotating the guidewire while simultaneously moving it proximally and distally. This action can cause damage to the fragile endothelial cell layer lining blood vessels. Additionally, conventional guidewires can lose their ability to be rotated when the flexible distal ends enter vessels of reduced diameter. Rotation of the guidewire following inserting the distal end into a vessel having a reduced diameter produces high frictional forces between the walls of the small vessels and the guidewire. A desirable device would therefore require reduced rotation and increased ability to advance in a forward or distal direction through tortuous anatomies.

Another undesirable characteristic of conventional guidewires is the inability to support a catheter at the flexible, tapered, distal end. When a catheter is advanced toward a vascular location in and close to a bifurcation, the catheter tends to proceed in a straight line rather than following the guidewire, defined as prolapse. Further, the natural pulsation of the vascular system of a living animal can cause a conventional guidewire to move into or out of the body during the procedure, thereby losing its distal location.

An additional disadvantage of a general use catheter is that it must be inserted into the body over a guidewire. Therefore, both a catheter and a guidewire must be used to reach a targeted site within the body. A single device that functions as an independent guidewire or both a catheter and a guidewire would save procedural time, reduce patient recovery time and cause less vascular damage to the patient.

Still another disadvantage related to current practices resides in the catheter itself. Conventional catheters typically have totally open distal ends. Manufacturers have made efforts to design catheters with soft distal ends to minimize the extent of vascular damage when the open end engages the interior wall of blood vessels. This scraping of the endothelial layer results in a triggering of the auto immune system, causing clots to form at the damage site. Also, the distal end of the catheter may become clogged with material removed from the interior wall of the blood vessels. It is apparent that this bolus of material will be expelled from the distal catheter end when another device is inserted through the catheter. An all-in-one device having a soft, closed distal end that opens to allow other devices to be deployed from the distal end and then re-closing when the devices are withdrawn, would resolve this problem.

Once the occlusion is reached, the objective is to cross the blockage with the guidewire or remove the guidewire and insert yet another device to cut through the occlusion. This is inherently disadvantageous in that additional time is required and a greater risk of vascular damage or perforation of the vessel wall is presented. Conventional devices used to cross the blockage are generally stiffer than conventional guidewires and when inside the catheter and reaching a bifurcation can cause the more flexible catheter to move away from the target site and follow the guide into the opposite branch of the bifurcation.

Physicians generally have four objectives when using such vascular devices: (1) To reach the occlusion; (2) To reach the occlusion without causing vascular damage; (3) To cross the occlusion once it is reached; and (4) To reach the occlusion and cross it in as little time as possible. A device able to accomplish all four objectives would be extremely advantageous. It is not uncommon for a physician to place a catheter somewhere in a vessel and exchange the first guidewire with one or more secondary guidewires having progressively stiffer distal ends to prevent prolapse of the devices placed over the guidewire(s). Yet another advantage would be having a guidewire stiff enough to be pushed and yet be directed into branched vessels with minimal torquing. Still another advantage would be a multi-function device able to carry a second device that could bore its way through an occlusion.

Vascular occlusions defined as Chronic Total Occulsions are blockages that can occur anywhere in a patient's vascular system, including coronary, carotid, renal, iliac, femoral, cerebral, popliteal and other peripheral arteries.

U.S. Pat. No. 4,676,249 to Arenas discloses a guidewire having a moving internal member to provide stiffness when required, but does not disclose a directable distal end or the ability to cross occlusions. Another U.S. Pat. No. 5,542,434, discloses a longitudinally movable core wire made of a memory metal alloy that stiffens when subjected to thermal energy. This allows the wire to become stiff and yet torquable when desired, but fails when a catheter needs to be slid over the device. Both devices are deficient when they reach an occlusion with heavily calcified plaque in that they do not have the ability to bore through the occlusion.

Using a conventional guidewire to reach the occlusion requires a catheter to be pushed over the guidewire, the final guidewire removed and then another device to be pushed through the catheter and used to cross the blockage. Such devices are generally known as percutaneous transluminal thrombectomy or artherectomy devices. These devices have various means to cross the occlusion and are singular devices lacking the ability to solely navigate the vasculature. As an example, one such device is disclosed in U.S. Pat. No. 6,945,951 and describes a thrombectomy catheter using high velocity saline through jets that erode away the blockage and cross an occlusion.

For all these and other reasons there is a clear need for a single device that can vary its distal end, is relatively stiff, has the ability to cross an occlusion and/or a feature that can drill or bore its way through an occlusion.

SUMMARY

In one aspect, the invention is directed to a vascular device including a shaft defining a longitudinal dimension, a lumen allowing fluid communication through the shaft extending along the longitudinal dimension and a proximal section and a distal section. The distal section further defines a weak side and a strong side and an actuating member is attached to the distal section, with the actuating member being capable of transmitting longitudinal force to the distal section. When longitudinal force is applied to the actuating member, the weak side of the distal section increases in size while the strong side maintains substantially the same size, resulting in the distal section deflecting.

In another aspect, the invention is directed to a vascular device including a shaft defining a lateral dimension, a longitudinal dimension, a proximal section, a distal section having greater flexibility than the proximal section and a lumen allowing access through the shaft extending along the longitudinal dimension. The shaft at least partly defines a coil, and the coil further defines a distal end. An actuating member is attached to the coil, and is capable of transferring longitudinal force to the coil. A side of the coil winds is physically connected, defining a connected side, which maintains the coil winds on the connected side in a constant configuration preventing differential spacing resulting from the application of longitudinal force and causing the connected coil winds to have a predetermined configuration in an unstressed state. When longitudinal force is applied to the actuating member, an unconnected side of the coil winds expands, resulting in the vascular device assuming a stressed configuration having a different shape than the vascular device in the unstressed configuration.

In a further aspect the invention is directed to a vascular device, including a shaft defining a lateral dimension, a longitudinal dimension, a proximal section, a distal section having greater flexibility than the proximal section and a lumen allowing access through the shaft extending along the longitudinal dimension. The shaft at least partly defines a coil, with the coil further defining a distal end. A flexible cutting shaft extends through the lumen and defines a proximal end and a distal end, with a cutting burr attached to the distal end of the cutting shaft. An actuating member is attached to the coil and is capable of transferring longitudinal force to the coil. A side of the coil winds is physically connected and defines a connected side, which maintains the coil winds on the connected side in a constant configuration preventing differential spacing resulting from the application of longitudinal force and causing the connected coil winds to have a predetermined configuration in an unstressed state. When longitudinal force is applied to the actuating member an unconnected side of the coil winds expands, resulting in the vascular device assuming a stressed configuration having a different shape than the vascular device in the unstressed configuration.

BRIEF DESCRIPTION OF THE DRAWINGS

FIG. 1A is a cross sectional centerline view taken along the longitudinal axis of the vascular device of FIG. 1, in a deflected configuration, following the application of distal force to the actuating member.

FIG. 1B is a cross sectional centerline view taken along the longitudinal axis of the vascular device of FIG. 1, in a deflected configuration, following the application of proximal force to the actuating member.

FIG. 4C is a cross sectional centerline view of the embodiment shown in FIG. 4 in a deflected configuration following the application of proximal force.

FIG. 5E shows a vascular device similar to that shown in FIG. 4, having an angled cutting shaft, in use during treatment.

DETAILED DESCRIPTION

Nomenclature

Figure 1:
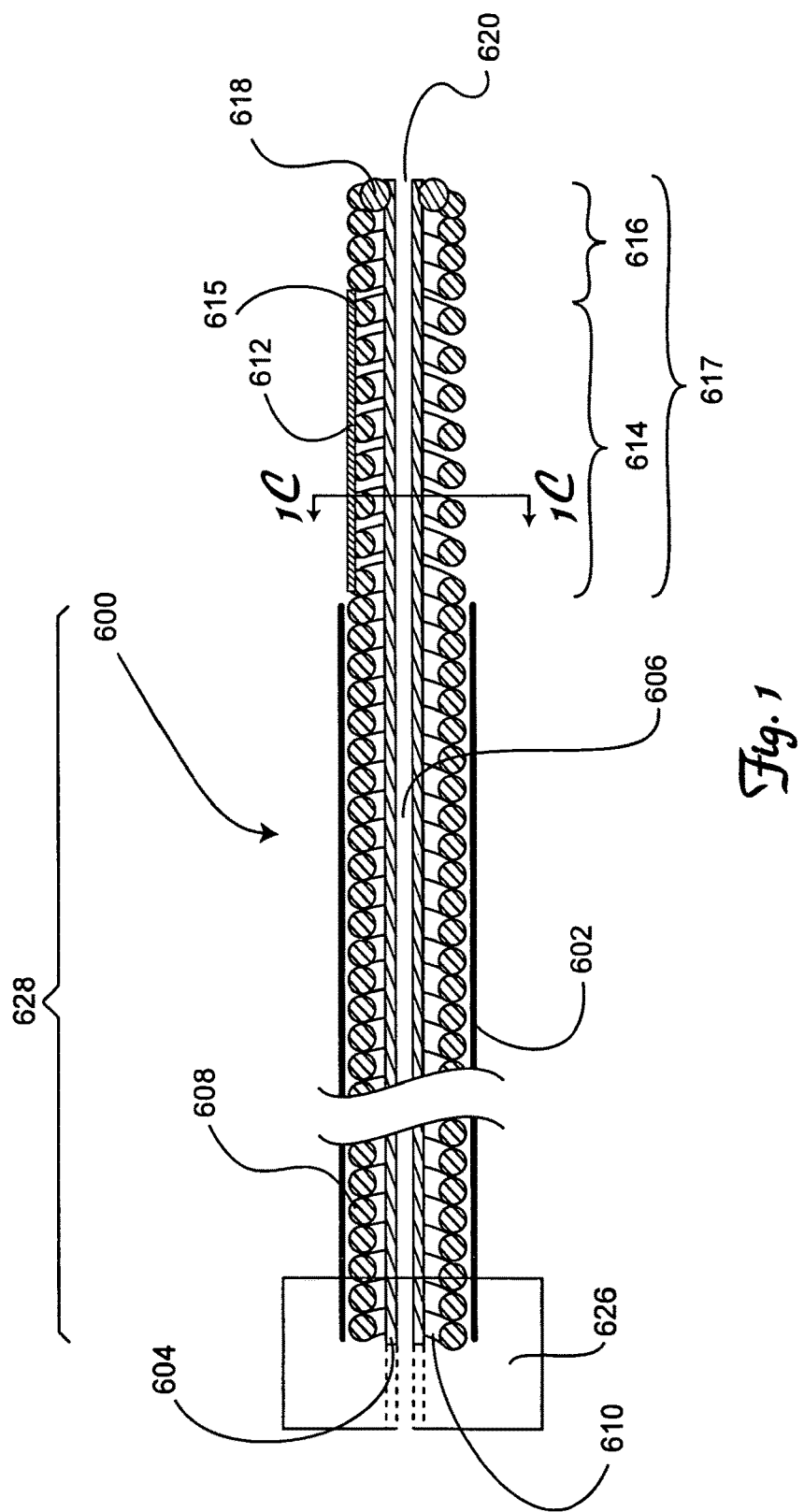
FIG. 1 is a cross sectional centerline view taken along the longitudinal axis of a vascular device of the present invention having a hollow actuating member.

50 Catheter
400 Vascular Device
402 Hollow Shaft
402a Proximal Termination of Hollow Shaft
402b Distal Termination of Hollow Shaft
404 Actuating Member
406 Coil
406a Open Wound Coil Section
406b Solid Coil Section
407 Distal Section
408 Weld
410 Distal Lumen Opening
412 Proximal End of Solid Coil Section
414 First Lumen
416 Second Lumen
418 Ribbon
420 Cutting Head
422 First Handle
423 Third Handle
424 Cutting Shaft
424a Proximal End of Cutting Shaft
424b Distal End of Cutting Shaft
425 Second Handle
426 Flattened Section of Coil
428 Solder
430 Non-Expandable Side
432 Expandable Side
500 Vascular Device
502 Hollow Shaft
504 Actuating Member
505 Sheath
506 Distal End (of Vascular Device)
508 Slit
510 Coil
510a Open Wound Coil Section
510b Solid Coil Section
512 Weld
514 First Lumen
516 Second Lumen
517 Distal Section
518 Ribbon
520 Cutting Head
524 Cutting Shaft
524a Proximal End of Cutting Shaft
524b Distal End of Cutting Shaft
526 Flattened Section of Coil
528 Solder
530 Non-Expandable Side
532 Expandable Side
534 First Handle
536 Second Handle
600 Vascular Device
602 Coating
604 Actuating Member
606 First Lumen
608 Coil
610 Second Lumen
612 Ribbon
614 Open Coil Section
615 Flattened Section of Coil
616 Distal Closed Coil Section
617 Distal Section (of Vascular Device)
618 Actuating Member Attachment
620 Distal First Lumen Opening
622 Non-Expandable Side
624 Expandable Side
626 Handle
628 Proximal Closed Coil Section
718 Cutting Shaft
720 Cutting Head
722 Angle in Cutting Shaft
1000 Vascular Vessel
1002 Vascular Obstruction
1002a Attached Obstruction
1002b Obstruction Debris
1400 Vascular Device
1410 Central Space
1412 Distal Section
1412a Loose Wound Section
1412b Tight Wound Section
1414 Coil
1415 Proximal Coil Section
1416 Flattened Section of Coil
1418 Ribbon
1420 Hollow Member
1422 Lumen
1424 Solder
1426 Coating
1428 Distal End of Vascular Device
1429 Proximal End of Coil
1430 Actuating Member
1432 Actuating Member Attachment
1434 Distal End of Coil
1436 Distal Lumen Opening
1438 Non-Expandable Side
1440 Expandable Side
1442 Handle Definitions "Anatomical Conduit" refers to a naturally occurring vessel or duct within a patient's body.

"Distal" means further from the point controlled by the operator (e.g., physician or technician) of a device.

"Distal Force" means force applied in a distal direction or toward a distal end of the device.

"ePTFE" means expanded polytetrafluoroethylene.

"FEP" means fluorinated ethylene-propylene.

"Handle" means a device used to grip certain components of the invention for the purpose of causing longitudinal movement of additional components.

"Longitudinal Force" means either distal force or proximal force.

"Prolapse" refers to an adverse event occurring when a medical device does not follow the desired path at a vascular bifurcation but instead where a relatively stiff device forces a relatively less stiff device straight through the vessel, pulling the less stiff device out of the side branch of the bifurcation.

"Proximal" means closer to the point controlled by the operator (e.g., physician or technician) of a device.

"Proximal Force" means force applied in a proximal direction or toward a proximal end of the device.

"PTFE" means polytetrafluoroethylene.

Construction

The following detailed description is to be read with reference to the drawings in which similar components in different drawings have the same nomenclature. The drawings, which are not necessarily to scale, show illustrative embodiments and are not intended to limit the scope of the invention.

It should be noted that combinations of materials and components described within this specification may be interchangeable and anyone skilled in the art will understand that a combination of materials or exchange of other materials to accomplish the work of the invention will not depart from the spirit of the invention. It is further understood that the invention is not limited to vascular use and can also be applied to use through an endoscope, gastroenterological procedures, laparoscope, artherectomy procedures, urological procedures or neurological procedures.

For the purpose of describing the actuation of the embodiments of the invention 600, 1400 as described below, a handle 626, 1442 is used. The function of the handle 626, 1442 is to contact the coated coil 608, 1414, move the actuating member 604, 1430 and provide greater control to the operator. Using the handle 626, 1442 allows the application of a longitudinal force (distal or proximal) from a proximal end (unnumbered) of the device 600, 1400 to the attached actuating member 604 and proximal force to the actuating member 1430, which causes a sliding motion. As described in detail below, the application of longitudinal force causes a distal section 617, 1412 of the vascular device 600, 1400 to deflect. In the cases of the embodiments of the invention 400, 500 a first handle 422, 534, contacts the hollow shaft 402, 502 and is attached to the actuating member 404, 504 allowing longitudinal force to be applied to the distal section 407, 517, causing it to deflect. A second handle 425, 536 is attached to a cutting head 420, 520 which distally extends from a distal lumen opening 410 or a sheath 505 and manually rotated in procedures requiring plaque removal.

FIG. 1 shows a cross sectional centerline view taken along the longitudinal axis of a vascular device 600 having a first lumen 606 and a second lumen 610. The vascular device 600 can be used as a guidewire or a catheter or as a combination of the two. The presence of a first lumen 606 and a second lumen 610 allows the device 600 to function as an aspiration device as well as a catheter so that during a medical procedure it can be simultaneously used to deliver other medical devices to a remotely navigated anatomical site and to aspirate fluids. The device 600 can also be used for the delivery of therapeutic fluids through the first lumen 606 to remote anatomical sites following navigation using the device 600 as a guidewire. The device 600 includes a coil 608 defining a proximal open coil section 614 and a distal closed coil section 616. A proximal closed coil section 628 extends proximally of a distal coil section 617 and is wound in a relatively closed coil configuration similar to the distal closed coil section 616. In one embodiment, the coil 608 can be made from a radiopaque material such as a platinum-nickel alloy that allows the physician to visualize the position of the coil 608 using radiological means, thereby navigating the vascular device 600 into desired anatomical pathways with minimal forward motion. In a manner similar to the other embodiments of the invention 400, 500 the device 600 is capable of deflecting by applying longitudinal force to an actuating member 604 which causes the expandable side 624 of the coil 608 to expand while the non-expandable side 622 is prevented from expanding by being fixedly attached to a ribbon 612 as explained below. The actuating member 604 can be made from a variety of materials having sufficient strength to be able to cause the distal section 617 to deflect and still be flexible enough to move with the coil 608, including but not limited to stainless steel alloys, nickel titanium alloys and reinforced polymeric materials such as Kevlar® or fabric materials. An outer polymer coating 602 covers the device 600 to the proximal point of attachment (unnumbered) of the ribbon 612, leaving the open coil section 614 exposed. The ribbon 612 is attached to the open coil section 614 at a flattened section 615. Means of attaching the ribbon 612 include but are not limited to adhesives, laser welding, or soldering. When negative pressure is applied to the second lumen 610 the device 600 can be used as an aspiration device to remove fluid or debris through the spaces between the open coil section 614, from an anatomical location the device 600 has been navigated to. The distal closed coil section 616 is close or tight wound and forms an area 618 for attaching a hollow actuating member 604. The actuating member 604 can be made from a variety of materials having sufficient strength to be able to cause the distal section 617 to deflect and still be flexible to flex enough to curve with the coil 608, including but not limited to stainless steel alloys, nickel titanium alloys and reinforced polymeric materials such as Kevlar® or fabric materials. The first lumen 606 which extends through the center of the actuating member 604 can also be used for aspirating fluids or debris when negative pressure is applied to the first lumen 606. Likewise, the first lumen 606 can be used for delivery of drugs or therapeutic fluids when positive pressure is applied. A coating 602 such as non-thrombogenic polymers, PTFE, ePTFE, FEP, polyester, polyurethane, polyethylene, silicone or hydrophilic may be applied over the proximal section (unnumbered) of the coil 608 to improve sterility as well as enhancing the outer smoothness of the guidewire 600, thereby causing less trauma to the patient during introduction, the procedure itself and removal. In one embodiment the coating 602 is applied to the coil 608 by applying a polymer heat shrink tubing such as a PTFE, FEP, or polyester, followed by the application of a proper amount of heat or an appropriate length of time. In additional embodiments the coating 602 is applied by dipping the guidewire 600 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 602 is a reduction in adverse reactions due to adhesion of platelets, proteins, cells or other fouling materials, which can cause fibrin clot production.

Figure 1C:
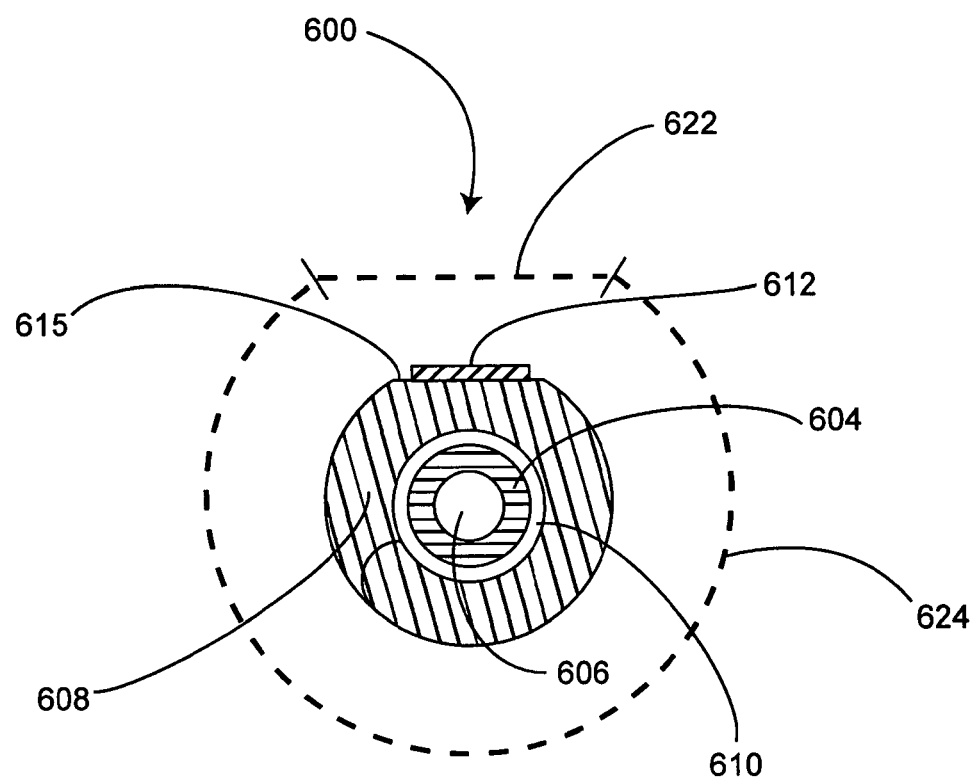
FIG. 1C is a lateral cross section view of the guidewire of FIG. 1 taken through the lines 1C-1C, illustrating the locations of the non-expandable side and expandable side.

When distal force is applied to the actuating member 604 by the operator, as shown in FIG. 1A, the distal section 617 deflects due to the non-expandable side 622 to which the ribbon 612 is attached being prevented from expanding while allowing the expandable side 624 to expand, resulting in the distal section 617 assuming a deflected configuration as best shown in FIG. 1A. As shown in FIG. 1B, if proximal force is applied to the actuating member 604 the distal section 617 is deflected in another direction than when distal force is applied. This is due to the pitch of the open wound coil section 614 having a relatively loose or open pitch to the coil winds (unnumbered), which allows the coil winds (unnumbered) on the expandable side 624, to be forced into a closer configuration. If the actuating member 604 is coupled with an actuating mechanism (not shown) such as a vernier type mechanism (not shown) a predictable and variable amount of deflection can be achieved with the application of a given amount of longitudinal force. FIG. 1C shows a lateral cross section of the vascular device 600 taken through the lines 1C-1C and illustrates the locations of the non-expandable side 622 and expandable side 624.

Figure 2:
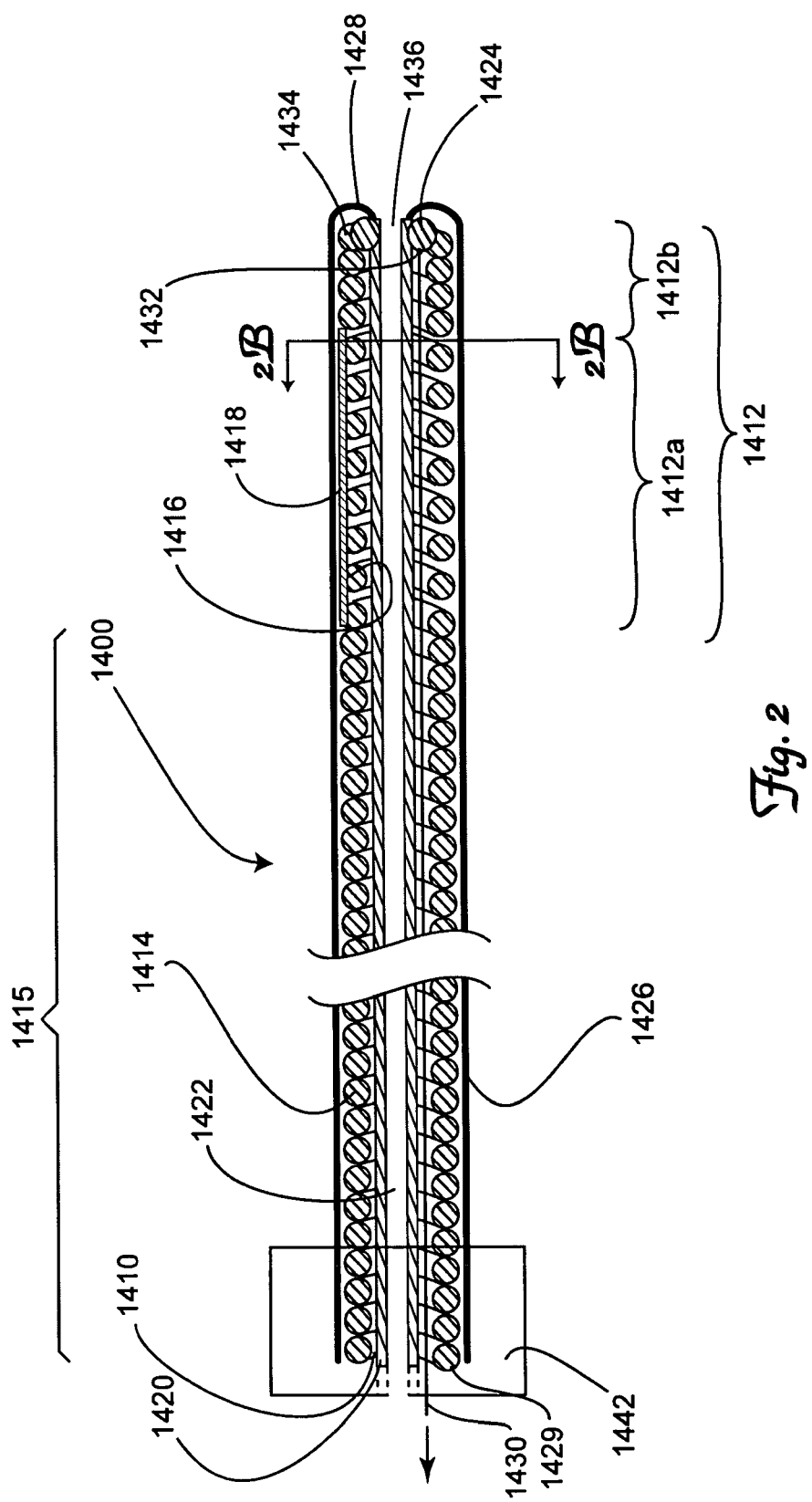
FIG. 2 is a cross sectional centerline view taken along the longitudinal axis of a vascular device of the present invention with a hollow conduit extending the length of the device and having a fibrous polymer or metal actuating member.

FIG. 2 is a cross sectional centerline view taken along the longitudinal axis of a vascular device 1400 of the present invention having a fibrous actuating member 1430 or metal actuating member (not shown) attached 1432 to a distal end 1434 of a coil 1414 enabling the vascular device 1400 to deflect to an alternative shape upon proximal force being applied to the actuating mechanism 1430. The vascular device 1400 can be used as a guidewire or a catheter or as a combination of the two. The device 1400 includes a coil 1414 defining a distal section 1412, further defining a loose wound section 1412a and a tight wound section 1412b. A proximal coil section 1415 extends proximally of the distal coil section 1412 and may be wound in a relatively closed coil configuration similar to the tight wound section 1412b. In one embodiment, the coil 1414 can be made from a radiopaque material such as a platinum-nickel alloy that allows the physician to visualize the position of the coil 1414 using radiological means, thereby navigating the vascular device 1400 into desired anatomical pathways with minimal forward motion. The coil 1414 extends between a distal end 1434 and a proximal end 1429 and defines a central space 1410 inside the coil winds. The coil 1414 defines a flattened section 1416 towards the distal end 1434 which is configured to receive a ribbon 1418 which is affixed to the coil 1414. The ribbon 1418 is made of a suitable metallic material such as austenitic stainless steel alloy or a tungsten alloy such as tungsten-molybdenum and tungsten-rhenium. In some instances, iridium is added to the alloy to increase strength and radiopaqueness. In another embodiment (not shown) the ribbon 1418 is not used and instead the deflectable distal section 1412 is defined by a series of welds (not shown), gluing (not shown) or mechanical fasteners (not shown) affixed to the coil winds. In an alternative embodiment (not shown), the ribbon 1418 is replaced by the application of a polymer fiber fused to coil 1414. The fiber (not shown) is entangled into the coil 1414 by means of weaving in and out of the coil winds and looping around the individual coil winds to form a solid attachment after application of an adhesive. The ribbon 1418 (or other means of securing) functions to bind together the portions of the coil 1414 to which it is attached to form a non-expandable side 1438 as best shown in FIG. 2B. Means of attaching the ribbon 1418 to the flattened section 1416 include but are not limited to adhesives, laser welding, or soldering. Thus, when proximal force is applied to the actuating member 1430 by the operator, the distal section 1412 will deflect due to the non-expandable side 1438 of the coil 1414 to which the ribbon 1418 is attached being prevented from expanding while allowing the expandable side 1440 to expand, resulting in the distal section 1412 deflecting from a straight configuration. If the actuating member 1430 is coupled with an actuating mechanism (not shown) such as a vernier type mechanism (not shown) a predictable and variable amount of deflection can be achieved with the application of a given amount of proximal force. It is also observed that along the distal section 1412 the coil 1414 defines a loose wound section 1412a where it is wound at a lesser or looser pitch than the remainder of the coil 1414, imparting a greater degree of flexibility to the distal section 1412. Attached by solder 1424 or other means to the coil 1414 at the distal end 1428 is a hollow member 1420 which resides inside the central space 1410 and extends the length of the vascular device 1400. The hollow member 1420 functions to add stiffness and stability to the vascular device 1400, while also defining a lumen 1422 which can be used for such purposes as drug delivery, aspiration or as a general catheter. The hollow member 1420 can be made from a variety of materials having sufficient strength to be able to cause the distal section 1412 to deflect and still be flexible enough to move with the coil 1414, including but not limited to stainless steel alloys, nickel titanium alloys and reinforced polymeric materials such as Kevlar® or fabric materials. The actuating member 1430 can be made of a polymeric material such as Kevlar® or other suitable metallic material such as stainless steel and is attached by solder 1424 or other means to the distal end 1434 of the coil 1414 and routed through the central space 1410 so as to be able to apply proximal force to the distal section 1412, allowing an operator to precisely deflect the distal section 1412 thereby enhancing the steerability and overall maneuverability of the vascular device 1400. A coating 1426 such as non-thrombogenic polymers, PTFE, ePTFE, FEP, polyester, polyurethane, polyethylene, silicone or hydrophilic may be applied over the coil 1414 to improve sterility as well as enhancing the outer smoothness of the guidewire 1400, thereby causing less trauma to the patient during introduction, the procedure itself and removal. In one embodiment the coating 1426 is applied to the coil 1414 by applying a polymer heat shrink tubing such as a PTFE, FEP, or polyester, followed by the application of a proper amount of heat or an appropriate length of time. In additional embodiments the coating 1426 is applied by dipping the guidewire 1400 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 1426 is a reduction in adverse reactions due to adhesion of platelets, proteins, cells or other fouling materials, which can cause fibrin clot production.

Figure 2A:
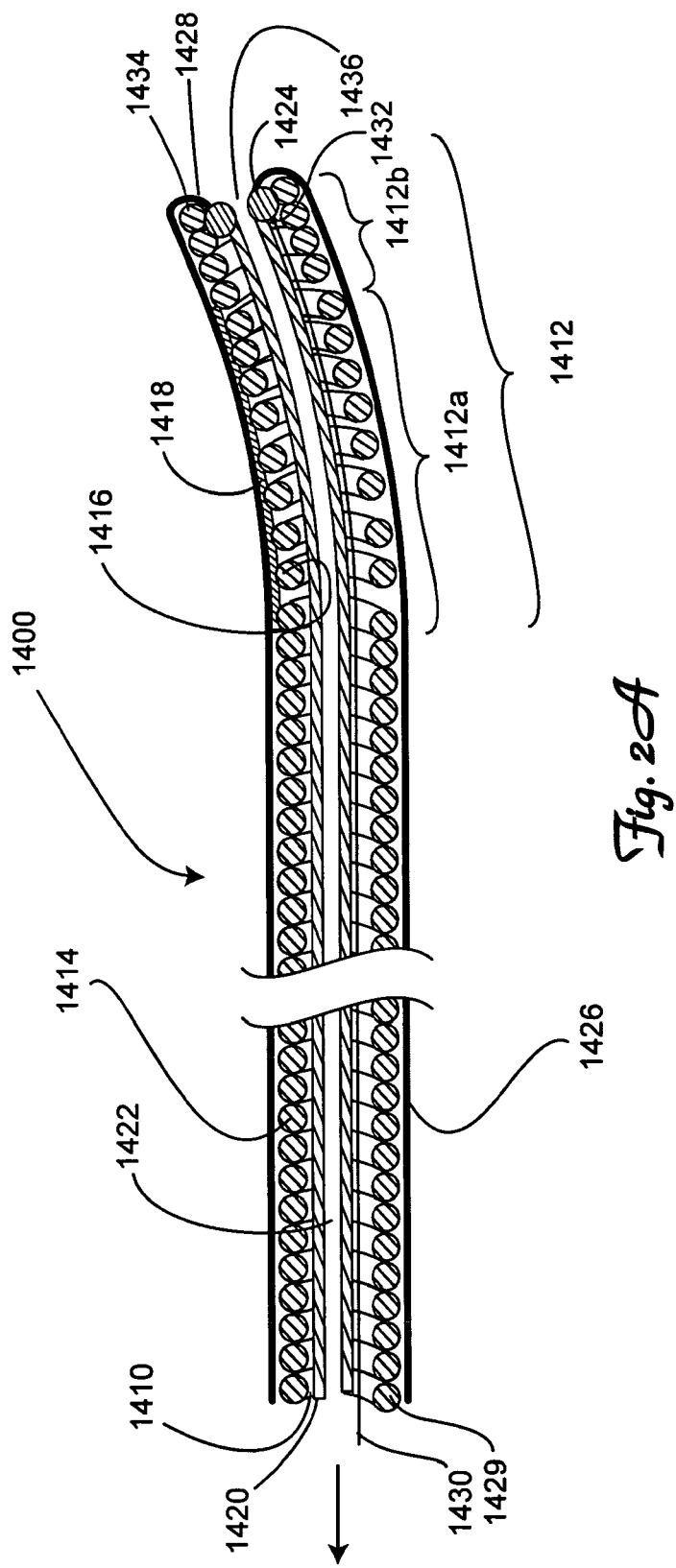
FIG. 2A is a cross sectional centerline view of the embodiment of the vascular device of FIG. 2 in a deflected configuration following the application of proximal force.
Figure 2B:
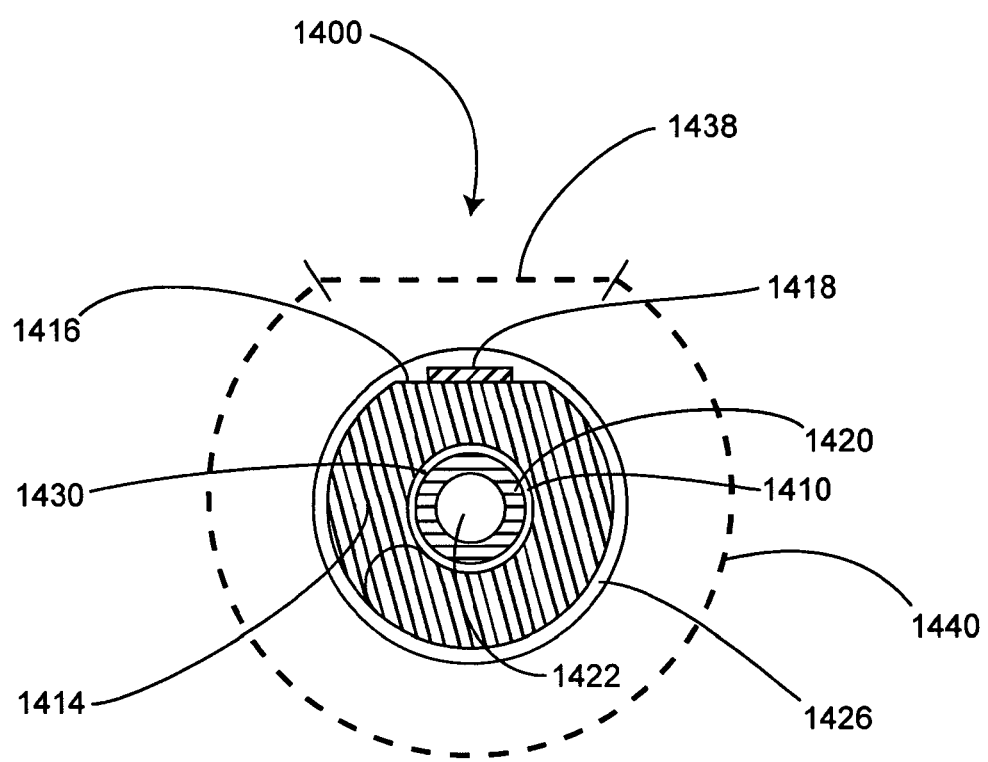
FIG. 2B is a lateral cross section view of the guidewire of FIG. 2 taken through the lines 2B-2B, illustrating the locations of the non-expandable side and expandable side.

As shown in FIG. 2A, if proximal force is applied to the actuating member 1430 the distal section 1412 is deflected. This is due to the expandable side 1440 being able to expand while the non-expandable side 1438 is prevented from expanding. If the actuating member 1430 is coupled with an actuating mechanism (not shown) such as a vernier type mechanism (not shown) a predictable and variable amount of deflection can be achieved with the application of a given amount of longitudinal force. FIG. 2B shows a lateral cross section of the vascular device 1400 taken through the lines 2B-2B and illustrates the locations of the non-expandable side 1438 and expandable side 1440.

Figure 3:
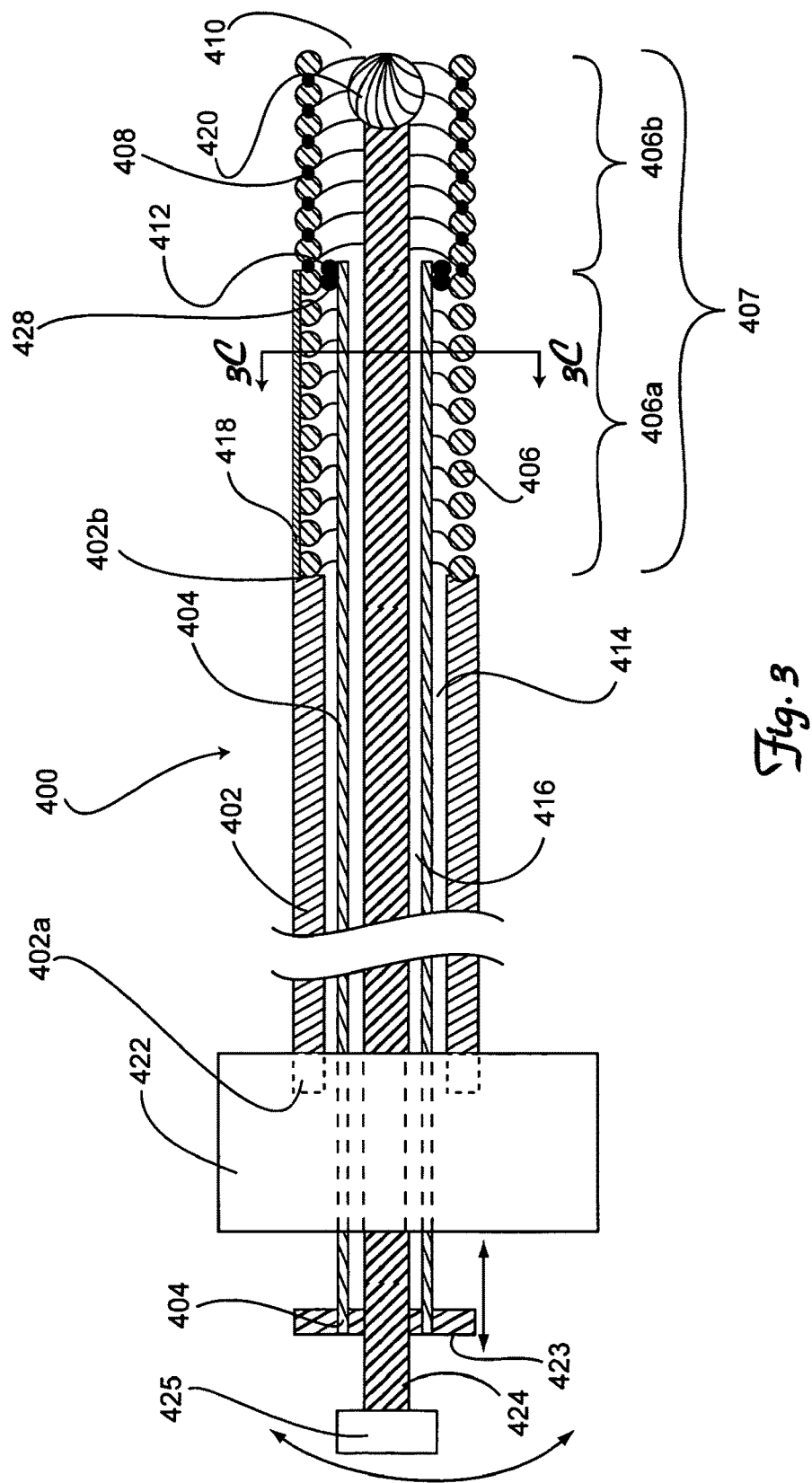
FIG. 3 is a cross sectional centerline view taken along the longitudinal axis of an alternative embodiment of the vascular device having a hollow actuating member, a handle and a cutting burr.
Figure 3A:
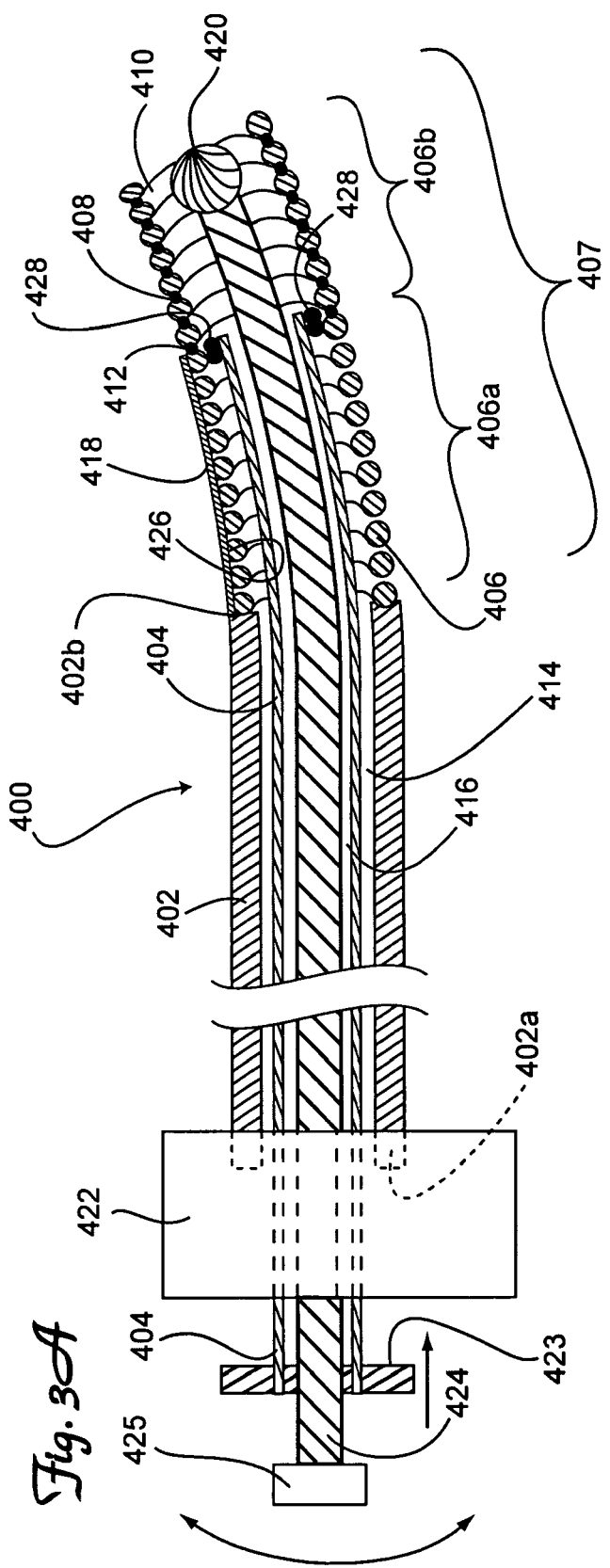
FIG. 3A is a cross sectional centerline view of the embodiment shown in FIG. 3 in a deflected configuration following the application of distal force.
Figure 3B:
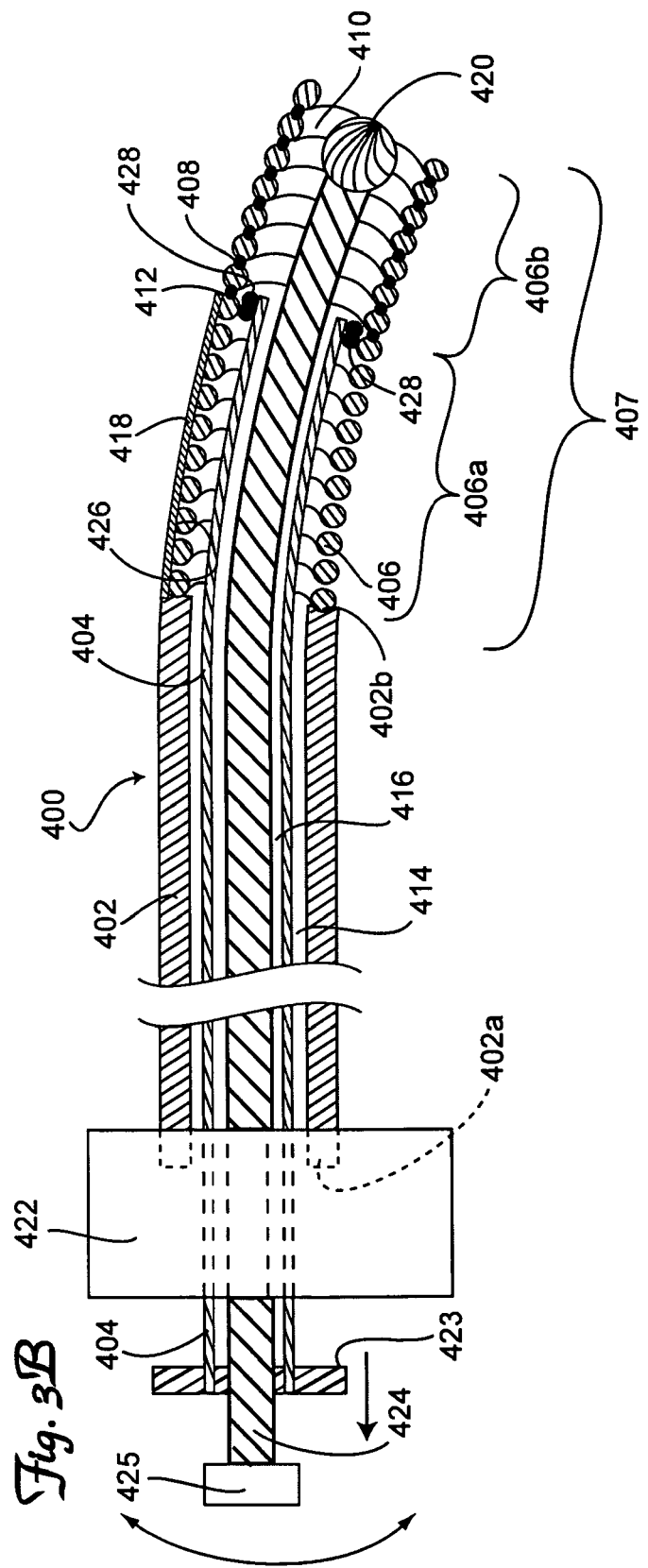
FIG. 3B is a cross sectional centerline view of the embodiment shown in FIG. 3 in a deflected configuration following the application of proximal force.

FIG. 3 shows a vascular device 400 which can be used as a guidewire or a catheter or as a combination of the two. A hollow shaft 402 defines a first lumen 414 into which is fitted an actuating member 404 which is itself hollow and defines a second lumen 416. The hollow shaft 402 is proximally attached to a first handle 422 which, as described above, is used to contact the device 400 as a whole. A third handle 423 is attached to the actuating member 404 which provides longitudinal control over the position of the actuating member 404. The hollow shaft 402 provides strength and support to the vascular device 400 and defines a proximal termination 402a, which is mounted within the first handle 422, and a distal termination 402b. The hollow shaft 402 and actuating member 404 can be made from a variety of materials having sufficient strength to be able to cause the distal section 407 to deflect and still be flexible enough to move with a coil 406, including but not limited to stainless steel alloys, nickel titanium alloys and reinforced polymeric materials such as Kevlar® or fabric materials. The coil 406 defines an open wound section 406a which is attached to and extends distally from the distal termination 402b of the hollow shaft 402 to the proximal end 412 of a solid coil section 406b. The open wound section 406a is further defined by the attachment of a ribbon 418 which in one embodiment is attached to a flattened section 426 of the coil 406. Means of attaching the ribbon 418 include but are not limited to adhesives, laser welding, or soldering. In one embodiment, the coil 406 can be made from a radiopaque material such as a platinum-nickel alloy that allows the physician to visualize the position of the coil 406 using radiological means, thereby navigating the vascular device 400 into desired anatomical pathways with minimal forward motion. The vascular device 400 defines a deflectable distal section 407 such that when longitudinal force is applied to the actuating member 404 by the operator, the distal section 407 deflects as a result of preventing the non-expandable side 430, to which the ribbon 418 is attached, from expanding, while allowing the expandable side 432 to expand, resulting in the distal section 407 assuming a deflected configuration as best shown in FIGS. 3A and 3B. The ribbon 418 is made of a suitable metallic material such as austenitic stainless steel alloy or a tungsten alloy such as tungsten-molybdenum and tungsten-rhenium. In some instances, iridium is added to the alloy to increase strength and radiopaqueness. In another embodiment (not shown) the ribbon 418 is not used and instead the deflectable distal section 407 is defined by a series of welds (not shown), gluing (not shown) or mechanical fasteners (not shown) affixed to the coil winds. In an alternative embodiment (not shown), the ribbon 418 is replaced by the application of a polymer fiber fused to the open wound coil section 406a. The fiber (not shown) is entangled into the open wound coil section 406a by means of weaving in and out of the coil winds and looping around the individual coil winds to form a solid attachment after application of an adhesive. The solid, distally located section 406b of the coil 406 is created by the presence of welds 408 between the individual coil winds (unnumbered) which function to prevent flexing of the solid section 406b from the application of longitudinal force. The solid coil section 406b terminates at a distal lumen opening 410 which is in fluid communication with the second lumen 416 and can thus be used to either deliver or aspirate substances from the anatomical area accessed by the device 400. The actuating member 404 extends proximally from the first handle 422 allowing access to the second lumen 416 and distally to the junction between the open wound section 406a and solid section 406b of the coil 406, where it is attached by solder 428. Extending through the second lumen 416 is a rotatably mounted, flexible cutting shaft 424, defining a proximal end 424a and a distal end 424b which terminates distally with a cutting burr 420 mounted thereon which is used to remove plaque or clots from a vessel. A second handle 425 is distally attached to the cutting shaft 424 and is manually rotated by the physician as needed, resulting in the cutting burr 420 simultaneously rotating. Flexibility of the cutting shaft 424 is preferably provided by making it of superelastic nitinol, but it is also contemplated to be made of stainless steel, glass-filled polymer or carbon-filled polymer.

Figure 3C:
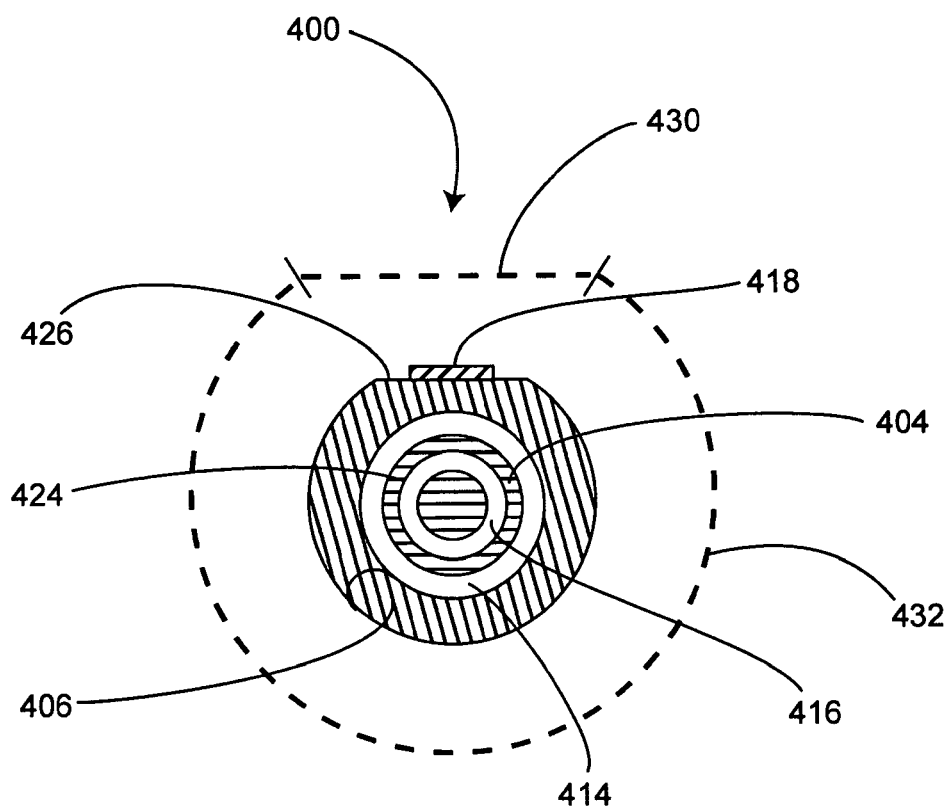
FIG. 3C is a lateral cross section view of the guidewire of FIG. 3 taken through the lines 3C-3C, illustrating the locations of the non-expandable side and expandable side.

When distal force is applied to the actuating member 404 by the operator, as shown in FIG. 3A, the distal section 407 deflects due to the non-expandable side 430 to which the ribbon 418 is attached being prevented from expanding while allowing the expandable side 432 to expand, resulting in the distal section 407 assuming a deflected configuration as best shown in FIG. 3A. As shown in FIG. 3B, if proximal force is applied to the actuating member 404 the distal section 407 is deflected in the opposite direction as when distal force is applied. This is due to the pitch of the open wound coil section 406a having a relatively loose or open pitch to the coil winds (unnumbered), which allows the coil winds (unnumbered) on the expandable side 432, to be forced into a closer configuration. If the actuating member 404 is coupled with an actuating mechanism (not shown) such as a vernier type mechanism (not shown) a predictable and variable amount of deflection can be achieved with the application of a given amount of longitudinal force. FIG. 3C shows a lateral cross section of the vascular device 400 taken through the lines 3C-3C and illustrates the locations of the non-expandable side 430 and expandable side 432.

Figure 4:
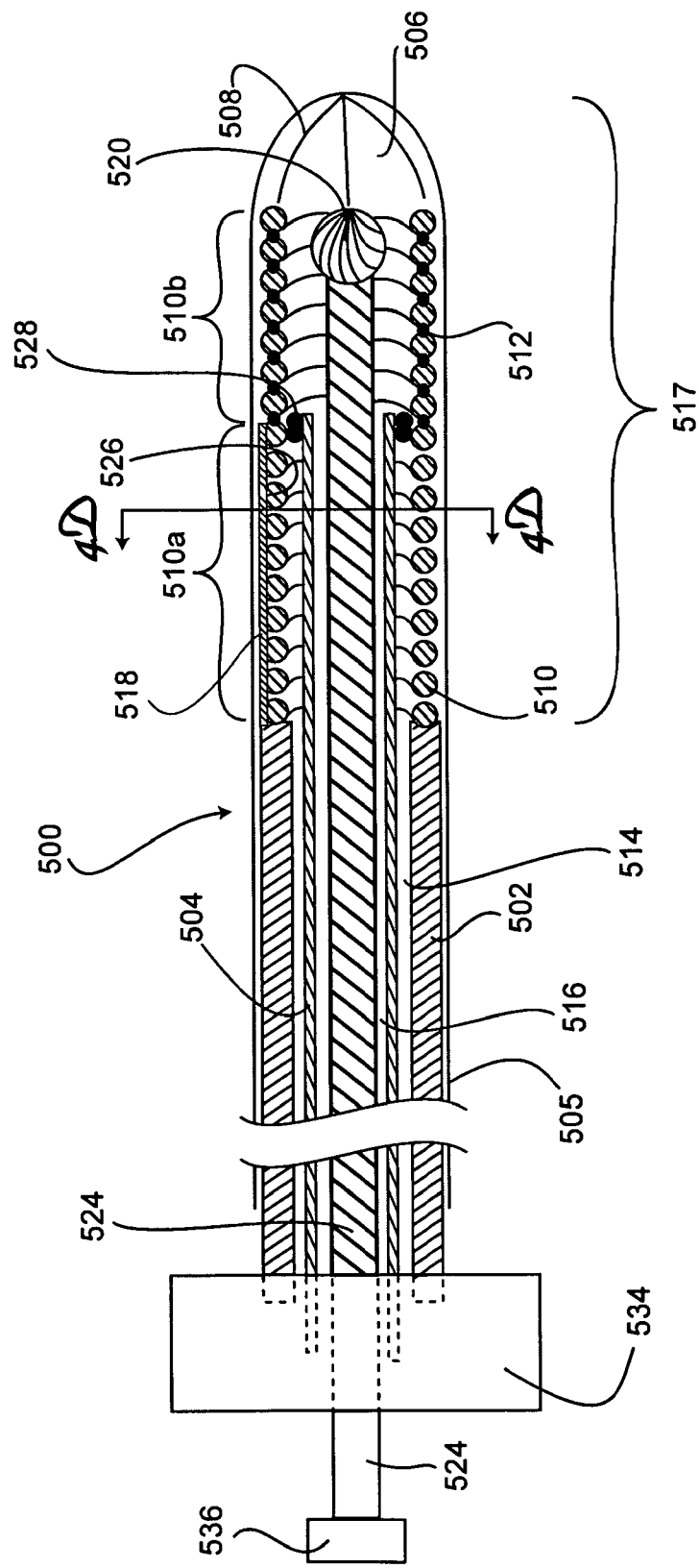
FIG. 4 is a cross sectional centerline view taken along the longitudinal axis of an alternative embodiment of the vascular device having a hollow actuating member, a handle and a cutting head which are covered by a sheath.
Figure 4A:
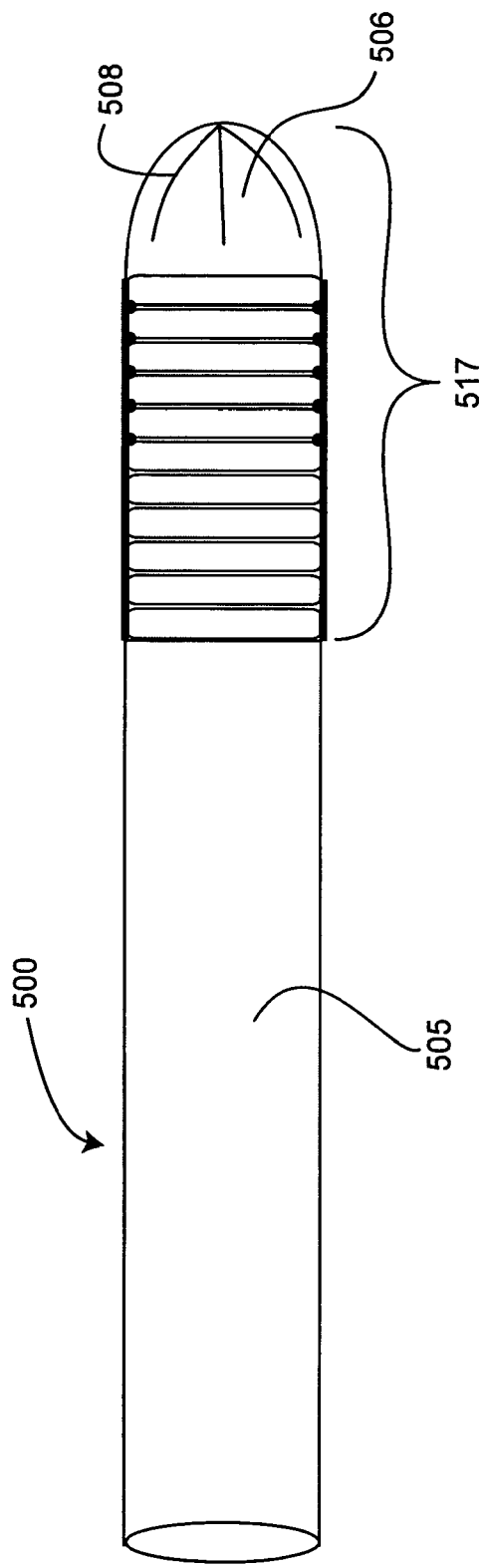
FIG. 4A is a side plan view of an embodiment of the vascular device shown in FIG. 4.

FIG. 4 is a cross sectional centerline view taken along the longitudinal axis of an alternative embodiment of the vascular device 500 which is similar to the embodiment of the vascular device 400 shown in FIGS. 3-3C, with the addition of a covering sheath 505. The vascular device 500 can be used as a guidewire or a catheter or as a combination of the two. The sheath 505 can be insert molded and surrounds at least the distal section 517 of the vascular device 500. The sheath 505 functions to make the device 500 more atraumatic, creating a safer device. A distal end 506 of the sheath 505 defines a range of at least one and up to eight slits 508 which are impressed across the center axis of the distal end 506 and which function to enclose a cutting head 520 and thereby protect delicate anatomical structures during introduction. When the cutting head 520 or other medical device (not shown) is deployed the slits 508 will open, becoming flaps (not shown), allowing the physician to perform a medical procedure, such as loosening and ultimately removing plaque from the interior surfaces of artery walls. When the cutting head 520 or other medical device (not shown) is pulled back into the second lumen 516 following completion of the procedure, the flaps 508 may close (not shown) or remain open still enclosing the cutting head 520, allowing the device 500 to be removed in a manner less likely to cause additional trauma to the patient.

As shown in FIG. 4 hollow shaft 502 defines a first lumen 514 into which is fitted an actuating member 504 which is itself hollow and defines a second lumen 516. The hollow shaft 502 and actuating member 504 are proximally attached to a first handle 534 which is used to contact the device 500 as a whole as well as allowing longitudinal control over the position of the actuating member 504. The hollow shaft 502 provides strength and support to the vascular device 500 as a whole and defines a proximal termination (unnumbered), which is mounted within the first handle 534. The hollow shaft 502 and actuating member 504 can be made from a variety of materials having sufficient strength to be able to cause the distal section 517 to deflect and still be flexible enough to move with a coil 510, including but not limited to stainless steel alloys, nickel titanium alloys and reinforced polymeric materials such as Kevlar® or fabric materials. The coil 510 defines an open wound section 510a which is attached to and extends distally from the distal termination (unnumbered) of the hollow shaft 502 to a proximal end (unnumbered) of a solid coil section 510b. The open wound section 510a is further defined by the attachment of a ribbon 518 which in one embodiment is attached to a flattened section 526 of the coil 510. Means of attaching the ribbon 518 include but are not limited to adhesives, laser welding, or soldering. In one embodiment, the coil 510 can be made from a radiopaque material such as a platinum-nickel alloy that allows the physician to visualize the position of the coil 510 using radiological means, thereby navigating the vascular device 500 into desired anatomical pathways with minimal forward motion. The vascular device 500 defines a deflectable distal section 517 so that when longitudinal force is applied to the actuating member 504 by the operator, the deflectable distal section 517 deflects, as described in detail below. The ribbon 518 is made of a suitable metallic material such as austenitic stainless steel alloy or a tungsten alloy such as tungsten-molybdenum and tungsten-rhenium. In some instances, iridium is added to the alloy to increase strength and radiopaqueness. In another embodiment (not shown) the ribbon 518 is not used and instead the deflectable distal section 517 is defined by a series of welds (not shown), gluing (not shown) or mechanical fasteners (not shown) affixed to the coil winds. In an alternative embodiment (not shown), the ribbon 518 is replaced by the application of a polymer fiber fused to the open wound coil section 510*a*. The fiber (not shown) is entangled into the open wound coil section 510*a* by means of weaving in and out of the coil winds and looping around the individual coil winds to form a solid attachment after application of an adhesive. The solid, distally located section 510*b* of the coil 510 is created in this embodiment by the presence of welds 512 between the individual coil winds (unnumbered) which function to prevent flexing of the solid section 510*b* from the application of longitudinal force. The solid coil section 510*b* terminates at a distal lumen opening (unnumbered) which is in fluid communication with the second lumen 516 and can thus be used to either deliver or aspirate substances from the anatomical area accessed by the device 500. The actuating member 504 extends proximally from the first handle 534 allowing access to the second lumen 516 and distally to the junction between the open wound section 510*a* and solid section 510*b* of the coil 510, where it is attached by solder 528. Extending through the second lumen 516 is a rotatably mounted cutting shaft 524, defining a proximal end 524*a* and a distal end 524*b* which terminates distally and is mounted with a cutting head 520 and is used to remove plaque or clots from a vessel. A second handle 536 is distally attached to the cutting shaft 524 and is manually rotated by the physician as needed, resulting in rotation of the cutting head 520. Flexibility of the cutting shaft 524 is preferably provided by making it of superelastic nitinol, but it is also contemplated to be made of stainless steel, glass-filled polymer or carbon-filled polymer.

Figure 4B:
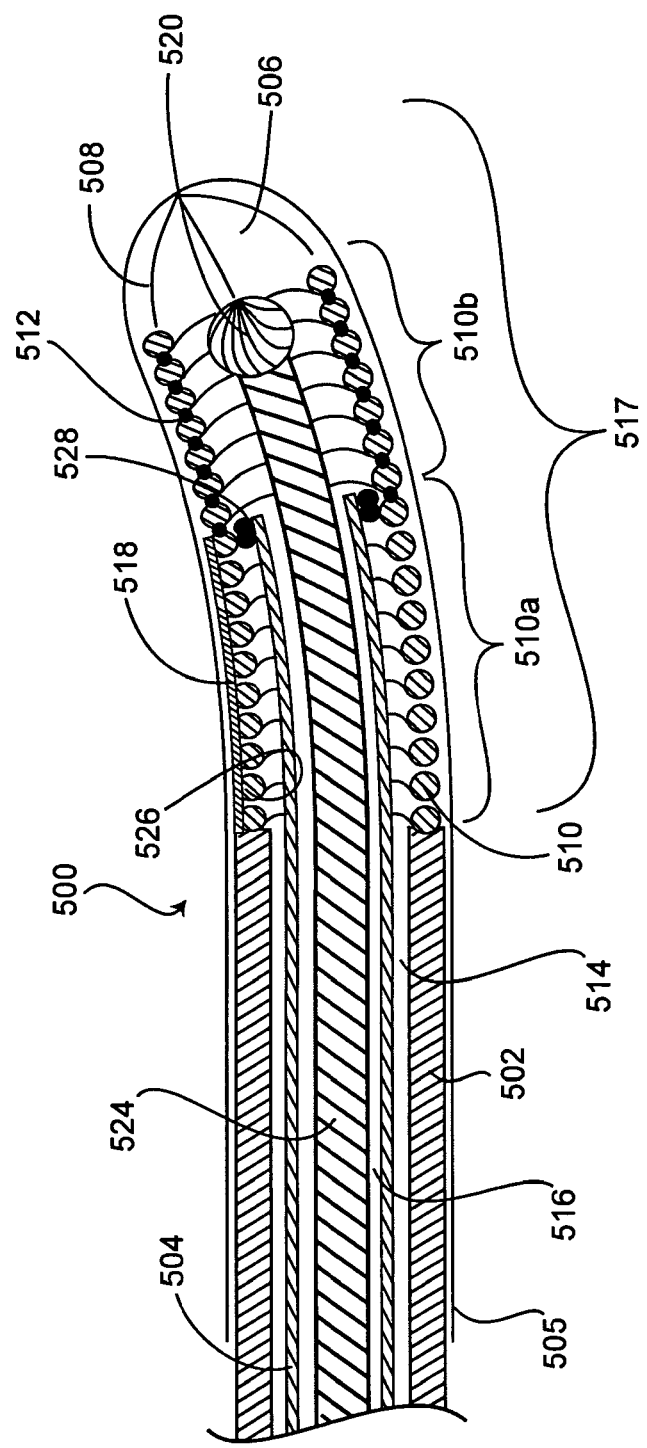
FIG. 4B is a cross sectional centerline view of the embodiment shown in FIG. 4 in a deflected configuration following the application of distal force.
Figure 4D:
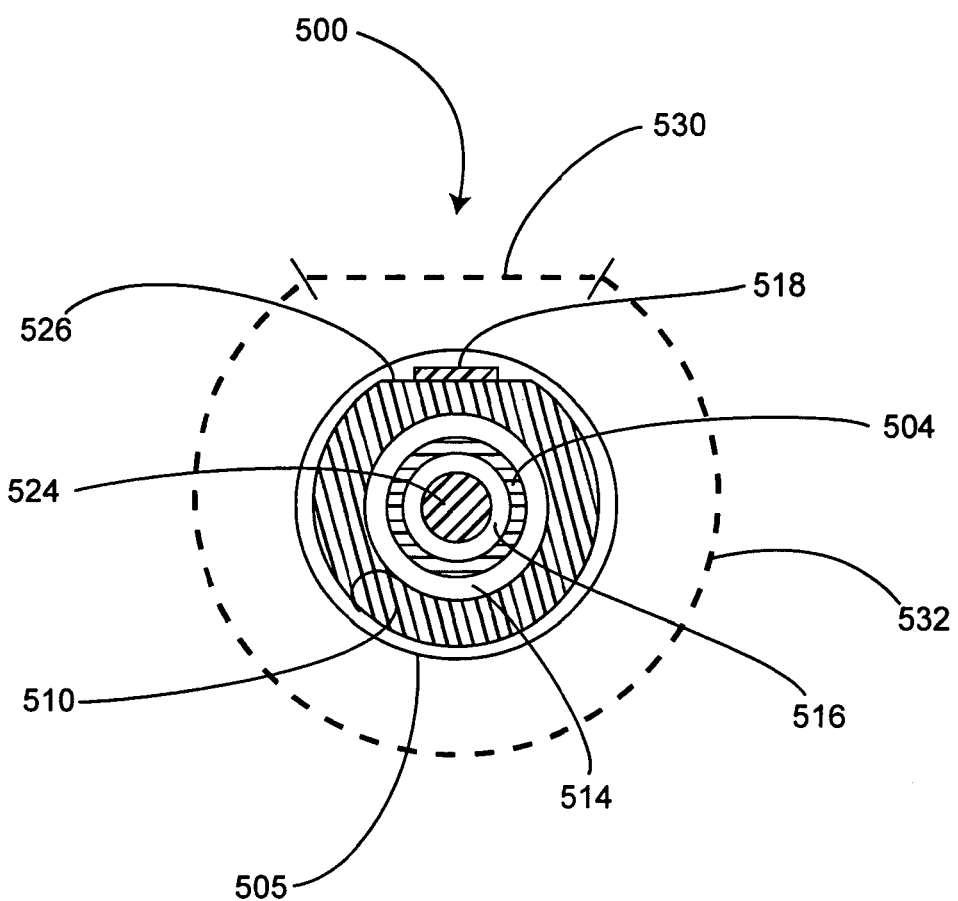
FIG. 4D is a lateral cross section view of the guidewire of FIG. 4 taken through the lines 4D-4D, illustrating the locations of the non-expandable side and expandable side.

When distal force is applied to the actuating member 504 by the operator, as shown in FIG. 4B, the distal section 517 deflects due to the non-expandable side 530 to which the ribbon 518 is attached being prevented from expanding while allowing the expandable side 532 to expand, resulting in the distal section 517 assuming a deflected configuration as best shown in FIG. 4B. As shown in FIG. 4C, if proximal force is applied to the actuating member 504 the distal section 517 is deflected in another direction as when distal force is applied. This is due to the pitch of the open wound coil section 510*a* having a relatively loose or open pitch to the coil winds (unnumbered), which allows the coil winds (unnumbered) on the expandable side 532, to be forced into a closer configuration. If the actuating member 504 is coupled with an actuating mechanism (not shown) such as a vernier type mechanism (not shown) a predictable and variable amount of deflection can be achieved with the application of a given amount of longitudinal force. FIG. 4D shows a lateral cross section of the vascular device 500 taken through the lines 4D-4D and illustrates the locations of the non-expandable side 530 and expandable side 532.

Figure 5A:
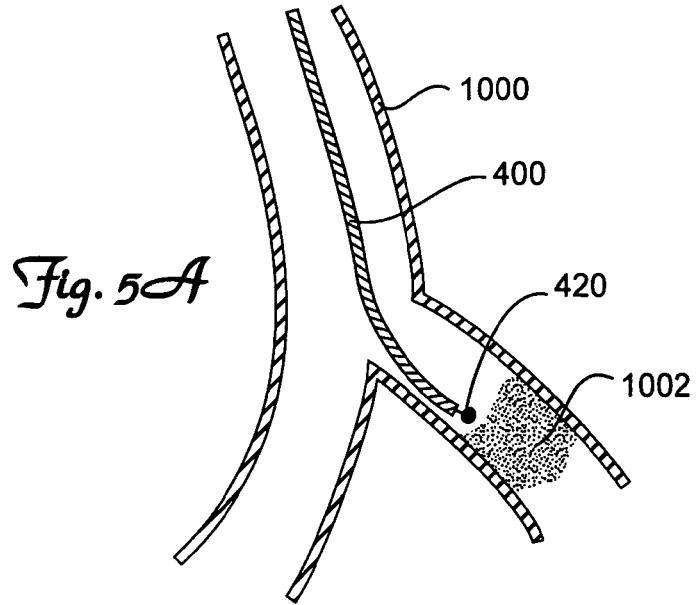
FIG. 5A shows the vascular device of FIG. 3 in use following introduction into a patient, approaching an obstruction at the onset of treatment.

FIG. 5A shows the vascular device 400 as shown in more detail in FIG. 3 in use following introduction into a patient, approaching an obstruction 1002 at the onset of treatment. It is seen that the device 400 has been navigated to the obstruction 1002 in a vessel 1000 which requires opening. Cutting head 420 has been deployed from the second lumen 416 to eventually bore through the obstruction 1002 and it is observed that the distal end (unnumbered this figure) of the device 400 is in the deflected configuration as a result of applying distal force to the actuating member 404 which allows the device to be precisely navigated through a tortuous vascular pathway.

Figure 5B:
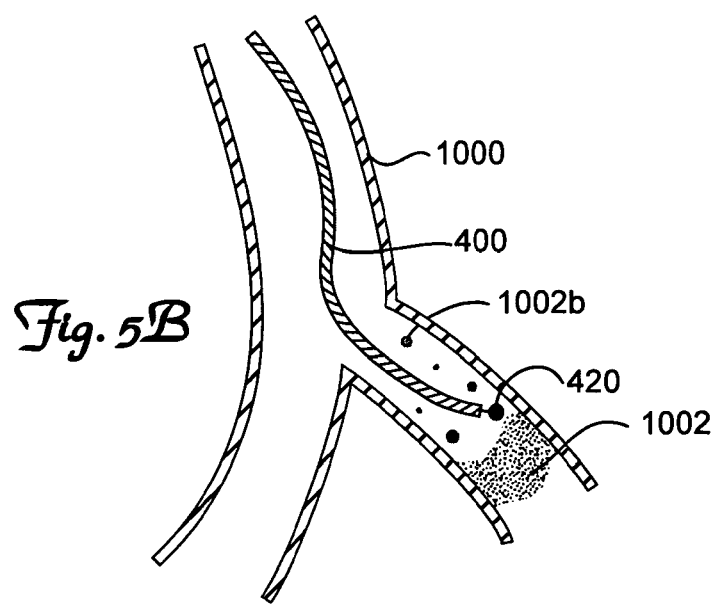
FIG. 5B shows the vascular device of FIG. 3 in use during treatment.

FIG. 5B shows the vascular device 400 in use during the beginning of treatment. It is seen that the deployed cutting head 420 is being rotated and contacting the obstruction 1002. It is further seen that some of the obstruction 1002*b* has been detached from its main body following treatment.

Figure 5C:
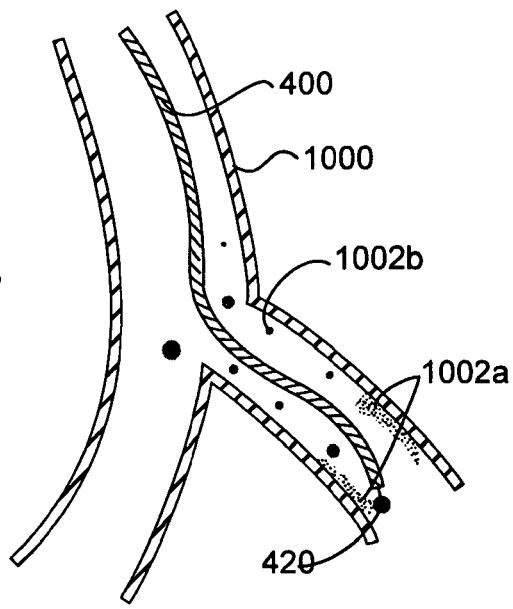
FIG. 5C shows the vascular device of FIG. 3 in use following completion of treatment.

FIG. 5C shows the vascular device 400 in use following completion of treatment. It is seen that the obstruction 1002 has been crossed and that some obstruction 1002*a* remains attached to the vessel 1000 wall while other obstruction 1002*b* is detached and has been removed.

Figure 5D:
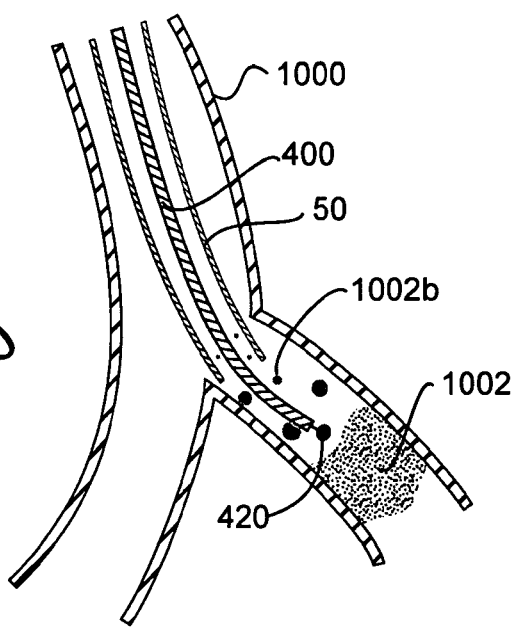
FIG. 5D shows the vascular device of FIG. 3 in use with the vascular device contained in a catheter used to aspirate debris from the treatment site.

FIG. 5D shows the vascular device 400 in use following introduction into a patient, approaching an obstruction 1000 at the onset of treatment, with the vascular device 400 contained in a catheter 50 used to aspirate debris from the treatment site.

FIG. 5E shows a vascular device 500 similar to that shown in FIG. 4 with an additional difference being a predetermined angle 722 formed into the cutting shaft 718. It is seen that the deployed cutting head 720 extends from the slit 508 at the distal end 506 of the sheath 505 and is being rotated and contacting the obstruction 1002. The angle 722 confers the advantage of allowing the physician to rotate the proximal end (not shown) of the actuating member (not shown) causing the cutting head 720 to move in an elliptical path around the inner walls of the vessel 1000, cutting and removing obstruction 1002. This allows the sheath 505 to remain stationary and not rotated by the physician. 500 and held in the center axis of the vessel 1000. This advantage also reduces the amount of vascular damage caused by required rotating of conventional guidewires or cutting devices by the physician in the process of navigating the device 500 through vascular obstructions.

The outer diameter of the vascular device 400, 500, 600, 1400 is manufactured to dimensions that are industry standards for certain medical procedures and can range from between approximately 0.006 inch to 0.121 inch which allows passage through a ten French catheter at 0.131 inch outer diameter, as an example. The length of the vascular device 400, 500, 600, 1400 is similarly manufactured to conform to industry standards and may range between approximately 10 centimeters to 300 centimeters as required by the particular medical procedure.

Use

Using the vascular device 400, 500, 600, 1400 of the present invention first requires removal from sterile packaging. Standard surgical techniques are employed to incise the proper blood vessel or bodily duct using an introducer having one or more sealed ports. The introducer can range in diameter from 4 to 24 French depending on the vessel or bodily duct size and location. Most procedures performed for Percutaneous Transluminal Coronary Angioplasty (PTCA) use a 6 to 10 French device passing through the introducer. A 6 to 10 French catheter having an open and blunt distal end can cause vascular damage passing through the vessels. Therefore one embodiment of the invention described herein discloses a rounded, bulleted distal end. The introducer is placed into the vessel lumen and is followed by insertion of a guidewire, catheter or other medical device that can pass transluminally through the vessel to the site of therapy. A rounded distal end will facilitate this task with less vascular damage.

The vascular device 400, 500, 600, 1400 is then inserted into the introducer and carefully navigated through the patient's vasculature until the treatment site is reached.

At that point, either the vascular device 400, 500, 600, 1400 is used to complete the procedure or another device is passed over or through the vascular device 400, 500, 600, 1400. At the completion of the procedure the vascular device 400, 500, 600, 1400 is disposed of.

In the embodiments 400, 500 as described above, the invention may be employed as a combination guidewire and thrombectomy or atherectomy device to remove calcified plaque or venous thrombosis. When these embodiments of the vascular device 400, 500 are used the physician places the distal end 410, 506 near the obstruction and a radio opaque contrast material may be injected into the artery through a lumen in the device, after which the physician advances a second handle 425, 536 at the proximal end (unnumbered) to deploy the cutting head 420, 520 at the distal end 410, 506 and slowly advance the device while manually rotating the second handle 425, 536. Aspiration may be used to remove the debris detached and displaced by the cutting head 420, 520. Upon completion of the procedure, the vascular device 400, 500 is removed and disposed of. These embodiments allow the physician to navigate a single device to the diseased area and complete the procedure in the shortest time with the least amount of vascular damage.

While the invention as described above can be used as a combination guidewire/thrombectomy/atherectomy device, it can also be used a catheter. Most transfemoral coronary catheterization employ between a 4 and 10 French catheter. Small arteries will utilize around a 4 French catheter while larger arteries could utilize up to a 10 French catheter. Cited by the Journal of the American Medical Association, upward of three million cardiac catheterizations are performed annually in the United States. A device to reduce procedural time vascular damage would be an economic advantage to the industry. The vascular device 400, 500, 600, 1400 may be applied to a variety of medical devices capable of being introduced into the vasculature or other anatomy of a patient. For example, the vascular device 400, 500, 600, 1400 could be applied to singular guidewires, guidewire/catheter combination (e.g., balloon angioplasty, stent deliver, drug delivery, fluid delivery or fluid removal), as a conduit for atherectomy devices and NUS catheters, laparoscopic and endoscopic devices, spinal or cranial navigation devices, neurostimulation and cardiac resynchronization leads, embolic protection devices, therapeutic devices and other medical devices. When used for drug delivery the invention finds utility by being able to remove fluid causing the surrounding area to lose excess fluid. A drug can then be injected and the affected area will more readily absorb the drug by the osmotic difference in pressure. This allows the drug to remain at the site rather than be carried away by the movement of interstitial fluids.

The vascular device 600, 1400 finds further utility in the implantation of neurostimulation or resynchronization leads which are typically 30 to 60 cm long. Currently these leads must include a large lumen for the insertion of a preformed stylet to steer the lead to the target site. As the industry continues to reduce the diameter of these leads to 4.1 French or less by removing the stylet lumen, a device is needed to steer the leads to the target site and allow the physician to rotate the lead (not shown) at the proximal end to implant the lead. The vascular device 600, 1400 accomplishes this by providing an open lumen from the proximal end (unnumbered) to the distal end 620, 1436 while allowing the distal end 620, 1436 to be manipulatively deflected by the physician and the proximal end of the lead manually rotated. Following implantation of the lead the invention is removed and disposed of.

The invention claimed is:

1. A vascular device, comprising:
   a flexible shaft having a lateral dimension, a length, a proximal section, a distal section having greater flexibility than the proximal section and a first lumen extending in a linear manner the length of the shaft and defining first and second open ends allowing unrestricted access between first and second open ends of the first lumen;
   a helical coil comprising a plurality of coil winds at least partly defining the shaft, the coil having an outermost periphery and a distal end;
   an actuating member capable of transferring longitudinal force to the coil, the actuating member defining a second lumen, with the first lumen between the helical coil and the actuating member; and
   at least two of the coil winds being physically connected at the outermost periphery of the coil by a fixing structure directly connected to the outermost periphery of the at least two of the coil winds, defining a connected side, to maintain the coil winds on the connected side in a constant configuration preventing differential spacing resulting from the application of longitudinal force and causing the connected coil winds to have a predetermined configuration in an unstressed state;
   wherein the application of longitudinal force to the actuating member causes an unconnected side of the coil winds to expand, resulting in the vascular device assuming a stressed configuration having a different shape than the vascular device in the unstressed state.

2. The vascular device of claim 1 wherein the actuating member is attached to a distal end of the distal section.

3. The vascular device of claim 1 wherein in a non-stressed configuration the vascular device has a straight configuration and applying distal force to the actuating member causes the distal section to deflect.

4. The vascular device of claim 1 wherein in a non-stressed configuration the vascular device has a straight configuration and applying proximal force to the actuating member causes the distal section to deflect.

5. The vascular device of claim 1 wherein the device in the unstressed state has a straight configuration and applying longitudinal force to the actuating member causes the distal section to deflect away from the longitudinal dimension.

6. The vascular device of claim 1 further comprising a flexible cutting shaft extending through the lumens, the cutting shaft having a distal end with a cutting burr attached to the distal end of the cutting shaft.

7. The vascular device of claim 6 wherein the cutting shaft is made of superelastic nitinol.

8. The vascular device of claim 6 wherein at least the distal end of the cutting shaft includes a sheath.

9. The vascular device of claim 1 wherein the at least two connected coil winds are physically connected by a metallic fixing structure attached directly to the outermost periphery of the coil.

10. The vascular device of claim 9 wherein the fixing structure is connected to an external flat section formed into the outermost periphery of the at least two connected coil winds.

11. The vascular device of claim 9 wherein the fixing structure is a ribbon having a rectangular cross section.

12. A vascular device comprising:
- a distal shaft section having an expandable side and a non-expandable side, the distal shaft section comprising a coil defining a first central space and comprising a plurality of coil winds, the plurality of coil winds defined by a first outer radius when viewed in a longitudinal direction and having an external flat section on the plurality of winds defined by a second outer radius when viewed in the longitudinal direction, the second outer radius being smaller than the first outer radius;
- a proximal shaft section defining a second central space coaxial with the first central space;
- a lumen defined by the first central space and the second central space, the lumen having first and second open ends allowing unrestricted fluid communication through the lumen;
- a fixing structure attached directly to the flat section on the outermost periphery of each of the plurality of coil winds; and
- an actuating member attached to the distal shaft section and capable of transferring longitudinal force to the coil.

13. The vascular device of claim 12 wherein the fixing structure is a ribbon having a rectangular cross section.

14. The vascular device of claim 12 further comprising a flexible cutting shaft extending through the lumen, the cutting shaft having a distal end with a cutting burr attached to the distal end of the cutting shaft.

15. The vascular device of claim 14 wherein the cutting shaft is made of superelastic nitinol.

16. The vascular device of claim 14 wherein at least the distal end of the cutting shaft includes a sheath.

* * * * *